(12) United States Patent
Hulliger et al.

(10) Patent No.: US 8,231,626 B2
(45) Date of Patent: Jul. 31, 2012

(54) SELF-RETAINING CABLE TIE

(75) Inventors: Urs Hulliger, Deitingen (CH); Bruno Laeng, Horriwil (CH)

(73) Assignee: Synthes USA, LLC, West Chester, PA (US)

( * ) Notice: Subject to any disclaimer, the term of this patent is extended or adjusted under 35 U.S.C. 154(b) by 182 days.

(21) Appl. No.: 12/771,517

(22) Filed: Apr. 30, 2010

(65) Prior Publication Data

US 2010/0292698 A1 Nov. 18, 2010

Related U.S. Application Data

(60) Provisional application No. 61/177,442, filed on May 12, 2009.

(51) Int. Cl.
*A61B 17/56* (2006.01)
*A61B 17/58* (2006.01)
*A61B 17/82* (2006.01)
*A61F 2/30* (2006.01)

(52) U.S. Cl. .......................................................... 606/74

(58) Field of Classification Search .................... 606/74, 606/139–141, 144–145, 148–151, 232, 263; 623/13.13–13.14
See application file for complete search history.

(56) References Cited

U.S. PATENT DOCUMENTS

| | | |
|---|---|---|
| 2,987,062 A | 6/1961 | Ellison |
| 3,111,945 A | 11/1963 | Von Solbrig |
| 3,469,573 A | 9/1969 | Florio |
| 4,119,091 A | 10/1978 | Partridge |
| 4,167,813 A | 9/1979 | Forster |
| 4,269,180 A | 5/1981 | Dall et al. |
| 4,272,870 A | 6/1981 | McCormick |
| 4,535,764 A | 8/1985 | Ebert |
| 4,667,662 A | 5/1987 | Titone et al. |
| 4,730,615 A | 3/1988 | Sutherland et al. |
| 4,813,416 A | 3/1989 | Pollak et al. |
| 4,896,668 A | 1/1990 | Popoff et al. |
| 5,190,545 A | 3/1993 | Corsi et al. |
| 5,355,913 A | 10/1994 | Green |
| 5,415,658 A | 5/1995 | Kilpela et al. |
| 5,462,542 A | 10/1995 | Alesi, Jr. |
| 5,496,318 A | 3/1996 | Howland et al. |
| 5,500,018 A | 3/1996 | Spotorlo et al. |
| 5,549,619 A | 8/1996 | Peters et al. |

(Continued)

FOREIGN PATENT DOCUMENTS

DE 3244680 6/1984

(Continued)

*Primary Examiner* — Kevin T Truong
*Assistant Examiner* — Sameh Boles
(74) *Attorney, Agent, or Firm* — Fay Kaplun & Marcin, LLP

(57) ABSTRACT

A system for securing a bone fixation device to a bone comprises a flexible longitudinal element configured to wrap about and stabilize one of a target portion of bone and a bone stabilizing element. The longitudinal element includes a plurality of projections extending distally from a first surface thereof. Each projection includes a proximal abutting surface in combination with a bone fixation element including a channel extending therethrough sized and shaped to slidably receive therein a portion of the longitudinal element distal of the head. The bone fixation element includes a recess shaped to receive the head and prevent the head from being drawn distally through the channel. The bone fixation element or the longitudinal element includes a tab configured to engage one of the proximal abutting surfaces to prevent the projections of the longitudinal element from moving proximally relative to the tab.

18 Claims, 2 Drawing Sheets

U.S. PATENT DOCUMENTS

| | | | |
|---|---|---|---|
| 5,571,105 A | 11/1996 | Gundolf | |
| 5,607,430 A | 3/1997 | Bailey | |
| 5,613,853 A | 3/1997 | Chasan et al. | |
| 5,665,088 A | 9/1997 | Gil et al. | |
| 5,665,089 A | 9/1997 | Dall et al. | |
| 5,683,404 A * | 11/1997 | Johnson | 606/151 |
| 5,766,218 A | 6/1998 | Arnott | |
| 5,772,663 A | 6/1998 | Whiteside et al. | |
| 5,810,824 A | 9/1998 | Chan | |
| 5,810,854 A | 9/1998 | Beach | |
| 6,050,998 A | 4/2000 | Fletcher | |
| 6,099,527 A | 8/2000 | Hochschuler et al. | |
| 6,302,889 B1 | 10/2001 | Keller | |
| 6,325,802 B1 * | 12/2001 | Frigg | 606/263 |
| 6,379,390 B1 | 4/2002 | Advani et al. | |
| 6,514,255 B1 | 2/2003 | Ferree | |
| 6,589,246 B1 | 7/2003 | Hack et al. | |
| 2001/0034522 A1 | 10/2001 | Frigg | |
| 2002/0177852 A1 | 11/2002 | Chervitz et al. | |
| 2004/0054409 A1 | 3/2004 | Harris | |
| 2005/0228375 A1 | 10/2005 | Mazda et al. | |
| 2005/0288674 A1 | 12/2005 | Golobek | |
| 2006/0058795 A1 | 3/2006 | Boyd | |
| 2006/0142772 A1 | 6/2006 | Ralph et al. | |
| 2006/0235401 A1 | 10/2006 | Baldwin et al. | |
| 2007/0093825 A1 | 4/2007 | Ferree et al. | |
| 2008/0234679 A1 | 9/2008 | Sarin et al. | |
| 2008/0300599 A1 | 12/2008 | Anapliotis et al. | |
| 2009/0012569 A1 | 1/2009 | Dall et al. | |

FOREIGN PATENT DOCUMENTS

| | | |
|---|---|---|
| DE | 3538645 | 5/1987 |
| DE | 4021246 | 1/1992 |
| DE | 4024334 | 2/1992 |
| DE | 4200757 | 7/1992 |
| DE | 4127550 | 2/1993 |
| DE | 19716504 | 12/1998 |
| EP | 0 009 327 | 4/1980 |
| EP | 0201905 | 11/1986 |
| EP | 0582857 | 2/1994 |
| EP | 0 608 592 | 8/1994 |
| EP | 0780096 | 6/1997 |
| EP | 0876798 | 11/1998 |
| FR | 2357229 | 2/1978 |
| FR | 2702951 | 9/1994 |
| FR | 2906704 | 4/2008 |
| GB | 2 257 913 | 1/1993 |
| GB | 2 414 936 | 12/2005 |
| WO | 88/06022 | 8/1988 |
| WO | 2006/062419 | 6/2006 |
| WO | 2006/136938 | 12/2006 |
| WO | 2007/010092 | 1/2007 |
| WO | 2007/036657 | 4/2007 |
| WO | 2008/146185 | 12/2008 |
| WO | 2009/013397 | 1/2009 |

* cited by examiner

SELF-RETAINING CABLE TIE

PRIORITY CLAIM

The present application claims priority to U.S. Provisional Application Ser. No. 61/177,442 entitled "Self-Retaining Cable Tie" filed on May 12, 2009, the entire disclosure of which is incorporated herein by reference thereto.

FIELD OF THE INVENTION

The present application relates to bone fixation and, more particularly, to bone cerclage systems and methods.

BACKGROUND

Fractures are often treated by wrapping a wire or other cable around a target portion of bone to stabilize the bone. The cable is typically looped around the target bone and locked at a desired tension to hold portions of bone in a desired spatial relation to one another. Known cables for this purpose are generally formed with bulky heads that lockingly engage elongated portions thereof to maintain the cable looped around a target portion of bone with a desired tension. However, the large profile of these locking heads often requires that they project away from the bone and any associated medical device (e.g., bone screw, bone plate, etc.) irritating ligaments, nerves and other adjacent tissue. Furthermore, once implanted, such cables often loosen and slide along the bone reducing the mechanical stability of the treated bone and increasing the possibility of further damage to the bone. Bone defects such as osteoporosis further increase the likelihood of such pen-prosthetic fractures. Loosening and/or movement of a cable may also result in misalignment of bone fragments, stiffness, nonunion, abnormal joint mechanics, healing impairment, etc.

SUMMARY OF THE INVENTION

The present invention is directed to a system for securing a bone fixation device to a bone comprising a flexible longitudinal element extending between a head at a proximal end thereof and a distal end, the longitudinal element being configured to wrap about and stabilize one of a target portion of bone and a bone stabilizing element, the longitudinal element including a plurality of projections extending distally from a first surface thereof, each projection including a proximal abutting surface in combination with a bone fixation element including a channel extending therethrough sized and shaped to slidably receive therein a portion of the longitudinal element distal of the head, the bone fixation element including a recess shaped to receive the head and prevent the head from being drawn distally through the channel, one of the bone fixation element and the longitudinal element including a tab configured to engage one of the proximal abutting surfaces preventing a portion of the longitudinal element on which the projections are formed from moving proximally relative to the tab.

DETAILED DESCRIPTION

Figure 1:
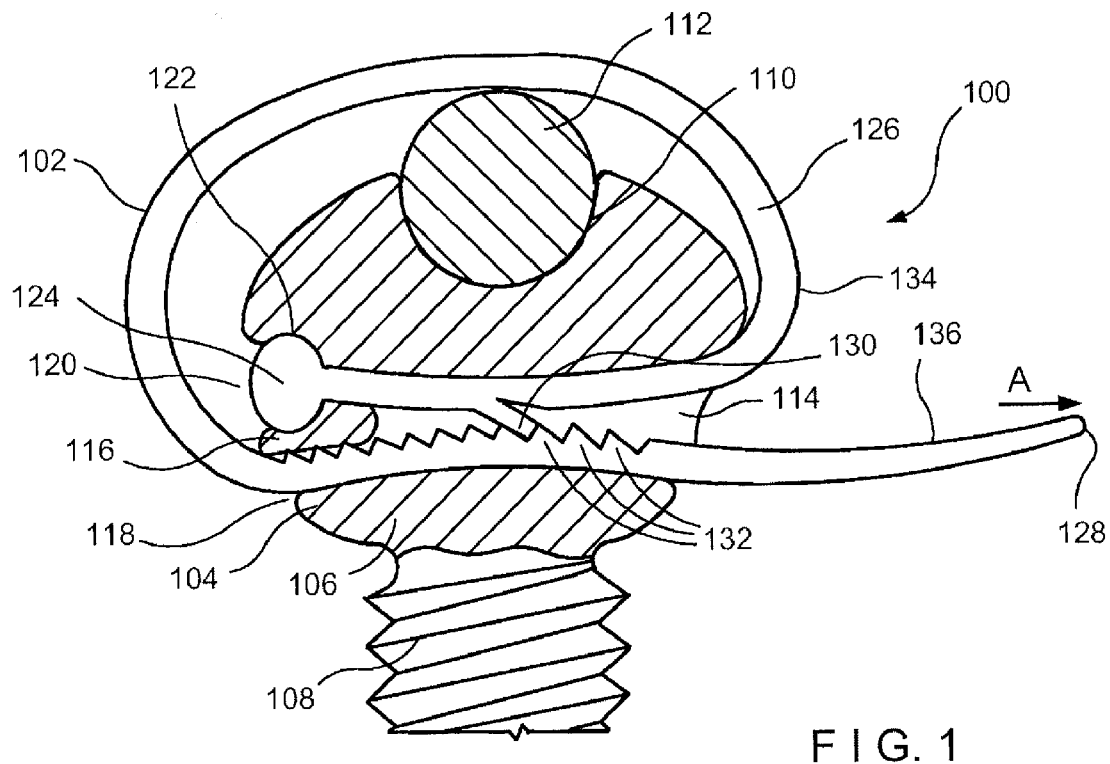
FIG. 1 shows a partial cross-section view of a system according to a first embodiment of the invention.

The present invention may be further understood with reference to the following description and the appended drawings, wherein like elements are referred to with the same reference numerals. The present invention relates generally to a system and method for the stabilization and fixation of fractured bones and bone fragments via cerclage. Specifically, the present invention relates to a cable tie with a minimal outer profile that is configured to lock the cable in a desired position about a target bone, with dimensions of the cable tie being selected to minimize or prevent the irritation of adjacent tissues. An exemplary cable tie according to the present invention is formed with self-locking notches formed on a body thereof to permit the cable tie to lock in place when positioned around a target portion of bone. Embodiments of the present invention may be employed with any of a plurality of procedures involving cerclage including bone fixation procedures and trolley spine procedures, as those skilled in the art will understand. It is further noted that exemplary system may be employed in any bone fixation procedure without deviating from the spirit and scope of the present invention. As used in this application, the terms proximal and distal refer to directions along the cable tie with a distal end including the sharpened tip which forms the leading end of the cable as it is inserted into the bone. The cable extends proximally from this end.

As shown in FIG. 1, an exemplary system 100 according to a first embodiment of the invention comprises a cable tie 102 mounted within a bone fixation device such as a bone screw 104. The screw 104 may be a pedicle screw configured for the fixation of a vertebral pedicle in accordance with a spinal fixation procedure, as those skilled in the art will understand. The screw 104 comprises a head 106 and a threaded shaft 108 configured for insertion into a target portion of a bone. The head 106 is formed with an arced recess 110 configured to engage a bone fixation rod 112. Those skilled in the art will understand that the bone fixation rod 112 is configured for attachment externally of the bone (not shown) in accordance with a spinal fixation procedure known in the art and described in greater detail below. The head 106 further comprises a channel 114 extending therethrough substantially perpendicular to a longitudinal axis of the threaded shaft 108, as those skilled in the art will understand. An abutment 116 is formed on a first end of the channel 114 defining two separated openings 118, 120 leading into the channel 114. The opening 120 further comprises a recess 122 configured to seat a head 124 of the cable tie 102 therein to minimize a profile of the head 106 extending out of the screw 104 without letting the head 124 pass through the channel 114, as will be described in greater detail hereinafter. The recess 122 may preferably be configured to house the substantially spherical head 124 of the cable tie 102 so that a proximal end thereof lies substantially flush with an outer surface of the head 124.

The cable tie 102 includes a longitudinal section 126 extending distally away from the head 124 to a distal end 128, a length of the cable tie 102 being chosen, for example, from any of a plurality of standard lengths known in the art and appropriate for a procedure to be performed. The cable tie 102 may be formed of any flexible yet durable material including, but not limited to, a compound plastic, polyaryletheretherketone ("PEEK"), or any other biocompatible plastic. The screw 104 can be formed of stainless steel or another biocompatible metal. The selected material for each of the cable tie 102 and the screw 104 may, for example, be chosen based on the expected load to be applied to each element during and after insertion to a target portion of bone. Although the head 124 is shown as substantially spherical, it may be formed in any desired shape without deviating from the spirit and scope of the present invention. Similarly, the recess 122 may be sized and shaped to accommodate a selected shape of the head 124.

In this embodiment, the longitudinal section 126 of the cable tie 102 is formed with a substantially rectangular cross-section, although other cross-sectional shapes are also envisioned. A first longitudinal wall 134 of the longitudinal section 126 comprises a tab 130 protruding distally therefrom at a predetermined angle. The tab 130 is separated from the head 124 by a predetermined distance along the longitudinal section 126 such that, in an operative configuration with the head 124 seated in the opening 120, the tab 130 is located within the channel 114. The longitudinal section 126 further includes a ribbed portion 132 including a series of teeth including ramped distal surfaces over which the tab 130 may slide while abutting proximal surfaces of the teeth lockingly engage the tab 130 to form a ratchet mechanism. The ribbed portion 132 extends along a predetermined length of the second longitudinal wall 136 sufficient to permit engagement thereof with the tab 130 after the cable tie 102 has been wound around a target structure and reinserted into the head 106 via the opening 118. A length of the ribbed portion 132 may optionally be selected to have a length substantially equivalent to or less than a length of the channel 114 so that the ribbed portion 132 does not irritate surrounding tissue. It is noted however, that the ribbed portion 132 may be formed of any length and may extend over any part of the longitudinal section 126 without deviating from the scope of the present invention.

In accordance with an exemplary method according to the present invention, one or more screws 104 are screwed into target portions of a bone (not shown). The rod 112 is then seated against the recess 110 of the screw 104 and temporarily held in place using any technique known in the art. The distal end 128 of the cable tie 102 is then inserted into the opening 120 through the head 106 of the screw 104 and out of the distal end of the channel 114 with the first longitudinal wall 134 including the tab 130 facing the shaft 108 of the screw 104. The longitudinal section 126 is then wound around the rod 112 and inserted into the opening 118 and through the channel 114. The cable tie 102 is then pulled in the direction A about the rod 112 to any desired tension using any known tensioning device and/or method. Application of this force causes the ribbed portion 132 to slide past the tab 130 and draws the head 124 into the recess 122 until it can move no further distally. Engagement of the tab 130 with the ribbed portion 132 in the manner of a ratchet locks a position of the cable tie 102 and maintains the desired tension thereon by preventing the distal end 128 from being retracted proximally into the channel 114. A distal portion of the cable tie 102 protruding out of the channel 114 may then be trimmed to lie substantially flush against the head 106 of the screw 104.

Figure 2:
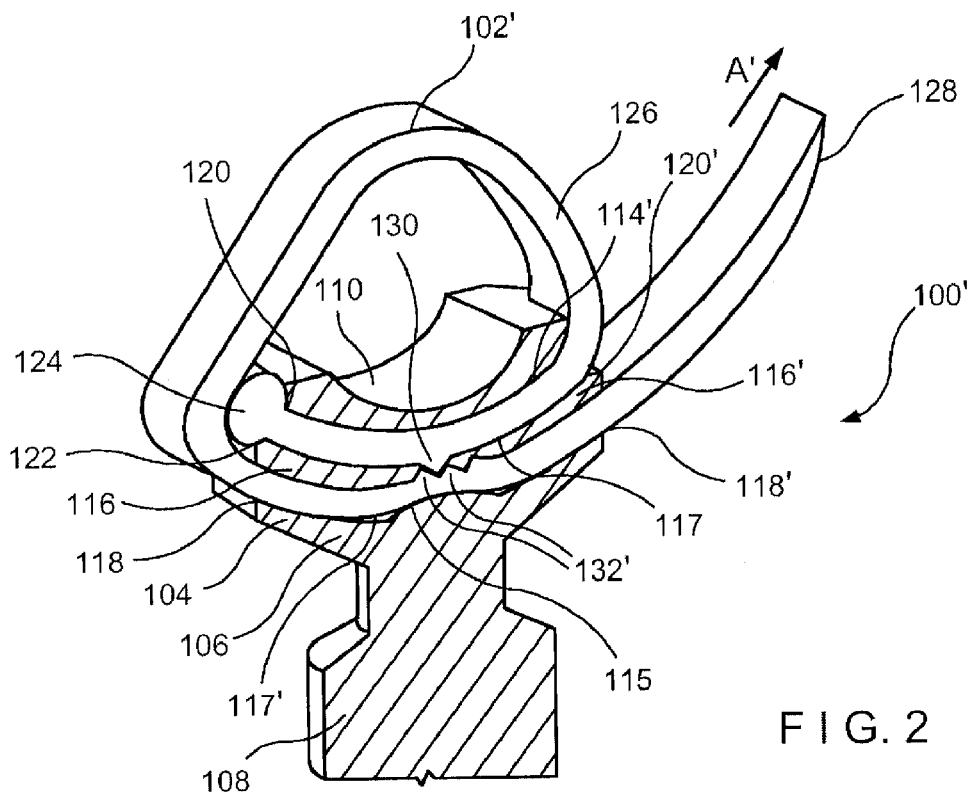
FIG. 2 shows a partial cross-sectional view of a system according to a second embodiment of the present invention.

FIG. 2 depicts a system 100' formed substantially similarly as the system 100 of FIG. 1 except as described below, wherein like elements are indicated with like reference numerals. The major difference between the system 100' and the system 100 is that a channel 114' of the system 100' is not perpendicular to a longitudinal axis of the bone screw 104 but rather, extends through the head 106 along an arced path. In the embodiment shown, the channel 114' follows an arced path with ends thereof facing away from the shaft 108. Thus, in order to tighten the cable tie 102' around the target anatomical structure (not shown), force is applied in the direction A' extending away from the shaft 108. In the head 106 of the bone screw 104 according to this embodiment, the abutment 116 is formed as a divider including proximal and distal sections 116, 116', respectively, separating the channel 114 into first and second sections 117, 117'. Thus, the proximal ends of the first section 117 of the channel 114' extends between the opening 120 and the opening 120' while the second section 117' extends between the openings 118 and 118'. The sections 116, 116' of the abutment 116 are separated from one another by a gap which opens the first and second sections 117, 117' to one another allowing adjacent portions of the cable tie 102' extending therethrough to abut one another. The second section 117' of the channel 114' may also include a bulge 115 aligned with the gap between the sections 116, 116' to urge the portion of the cable tie 102' passing thereover through the gap into contact with the adjacent portion of the cable tie 102'. An exemplary method for the system 100' remains substantially the same as the method disclosed above with respect to FIG. 1. If desired, the ribbed portion 132' of a cable tie 102' for use with the system 100' may be made shorter to the extent it can be ensured that the ribbed portion 132' will be in alignment with the gap between the sections 116, 116' when the cable tie 102' has been set at the desired tension in the manner described above.

Figure 3:
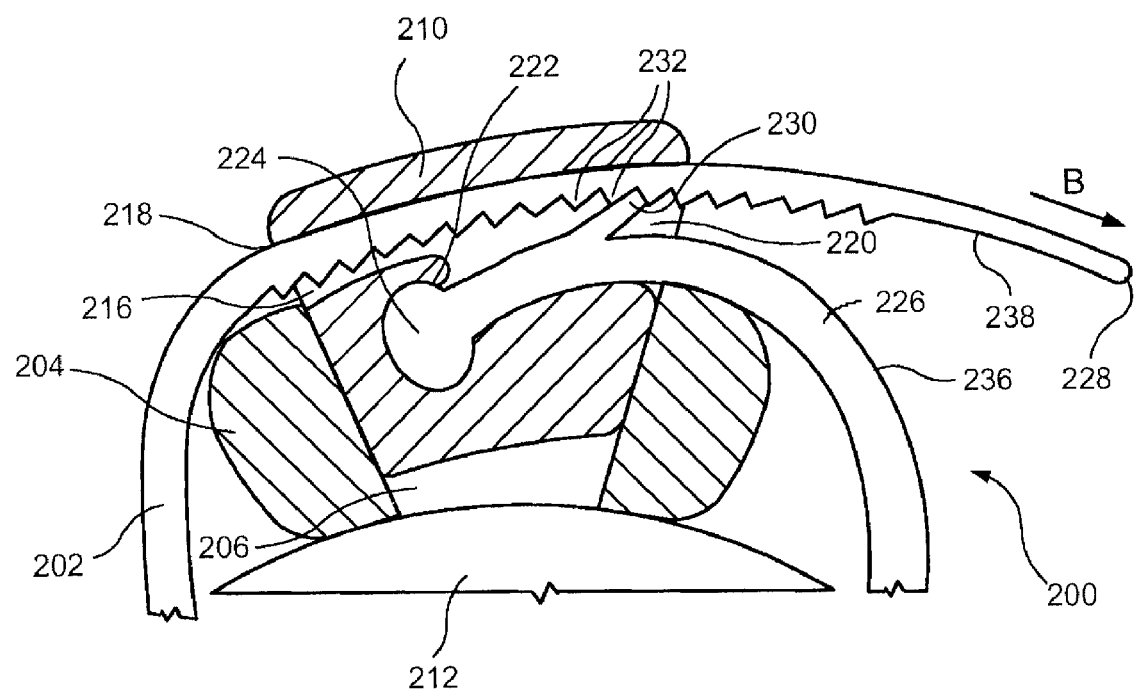
FIG. 3 shows a partial cross-sectional view of a system according to a third embodiment of the present invention.

As shown in FIG. 3, a system 200 according to a third exemplary embodiment of the present invention comprises a cable tie 202 formed substantially similarly to the cable tie 102 of FIG. 1. In the system 200, the cable tie 202 engages a bone plate 204 instead of a bone screw as described in earlier embodiments. The cable tie 202 comprises a longitudinal section 226 extending distally from a head 224 formed at a proximal end of the cable tie 202 to a distal end 228. A first longitudinal wall 236 of the cable tie 202 comprises a tab 230 configured to engage one of the ribs of the ribbed portion 232 formed on a second longitudinal wall 238. The tab 230 and ribbed portion 232 are configured to lockingly engage one in the same manner described above in regard to the cable tie 102 after the head 224 has been locked within a plate hole 206 of the bone plate 204 and the longitudinal section 226 has been wrapped around a target portion of bone as will be described in greater detail hereinafter. The plate hole 206 extends through the bone plate 204 from a top surface thereof to a bottom surface which, when in an operative position, contacts the bone 212. The plate 204 extends along the bone, for example, along a longitudinal axis substantially perpendicular to an axis of the plate hole 206. The plate hole 206 is tapered so that a diameter of a bottom end (i.e., an end adjacent to a surface of the bone 212) is smaller than a diameter at a top end thereof. It is noted, however, that the plate hole 206 may be formed with any desired dimensions and at any desired angle through the bone plate 204 without departing from the scope of the invention.

A locking block 210 received within the plate hole 206 via for example, a threaded or friction fit engagement extends along an axis substantially aligned with the axis of the plate hole 206 so that, in an operative configuration, the locking block 210 is substantially centered therewithin. The locking block 210 further comprises a channel 216 extending therethrough at an angle substantially perpendicular to its axis. The channel 216 which extends through the locking block 210 and is open at first and second ends 218, 220 thereof. The first end of the channel 216 is preferably wide enough to permit a single strand of the cable tie 202 to pass therethrough, as will be described in greater detail hereinafter while the second end 220 of the channel 216 is sized to receive two instances of the cable tie 202 therethrough side-by side. The channel 216 further comprises a recess 222 configured to lockingly engage the head 224 of the cable tie 202 so that the head 224 cannot be pulled out of the recess 222 when the cable tie 202 is tensioned. For example, the recess 222 may have an enlarged end into which the head 224 may be slid and a smaller slot extending therefrom so that, as the cable tie 202 and the head 224 are moved from the enlarged end of the recess 222 laterally into the slot, the head 224 is prevented from moving distally out of the slot.

In accordance with an exemplary method of use of the system 200, a bone plate 204 is first positioned in a desired orientation against a target portion of the bone 212. The head 224 of the cable tie is then lockingly inserted into the recess 222 and the locking block 210 is inserted into the opening 214 so that first and second ends 218, 220 of the channel 216 remain accessible to a user. The distal end 228 of the cable tie 202 is then drawn around the target portion of the bone 212 until the distal end 228 is adjacent to the first end 218 of the channel 216. As will be described in greater detail in a later embodiment, the distal end 228 of the cable tie 202 is then inserted into the channel 216 via the first end 218 with the ribbed portion 323 facing the tab 230. The distal end 228 is then drawn out of the head 224 in the direction of arrow B with the tab 230 ratcheting over the ribbed portion 232 until a desired tension is placed on the cable tie 202. The distal end 228 is then inserted into the first end 218 of the locking block 210 and through the channel 216. Engagement of the tab 230 with the ribbed portion 232 locks the cable tie at the desired position and tension and prevents any loosening thereof. Since the tab 230 and the ribbed 232 are housed within the channel 214, external forces applied to the locking block 210 (e.g., due to normal wear, etc.) do not compromise the position of the cable tie 202 around the bone, as those skilled in the art will understand.

It is noted that although the present embodiment has been described with a locking block 210 inserted through a bone plate 204, the locking block 210 may also be employed in a bone screw or other bone fixation device without deviating from the spirit and scope of the present invention.

It will be apparent to those skilled in the art that various modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. A system for securing a bone fixation device to a bone, comprising:
   a flexible longitudinal element extending between a head at a proximal end thereof and a distal end, the longitudinal element being configured to wrap about and stabilize one of a target portion of bone and a bone stabilizing element, the longitudinal element including a plurality of projections extending distally from a first surface thereof, each projection including a proximal abutting surface; and
   a bone fixation element including a channel extending therethrough sized and shaped to slidably receive therein a portion of the longitudinal element distal of the head, the bone fixation element including a recess shaped to receive the head and prevent the head from being drawn distally through the channel, one of the bone fixation element and the longitudinal element including a tab configured to engage one of the proximal abutting surfaces preventing a portion of the longitudinal element on which the projections are formed from moving proximally relative to the tab.

2. The system of claim 1, wherein the projections include ramped distal surfaces to slidingly engage the tab as a ratchet, distal movement of a distal portion of the longitudinal element drawing the projections over the tab to define a new proximal-most position of the distal portion of the longitudinal element as each projection moves distally past the tab to engage the abutting surface of corresponding the projection.

3. The system of claim 1, wherein the tab is formed on a portion of the longitudinal element which, when in an operative configuration around a target portion of bone, is received within the channel.

4. The system of claim 3, wherein the tab is formed on a first surface of the longitudinal element which is located on a side of a longitudinal axis of the longitudinal element opposite a second surface on which the projections are formed.

5. The system of claim 1, wherein the channel is sized to receive two thicknesses of the longitudinal element adjacent to one another with the first and second surfaces facing one another.

6. The system of claim 5, wherein the channel includes a divider separating a first lumen in which a proximal portion of the longitudinal element is received from a second lumen into which a distal portion of the longitudinal element is inserted after being wrapped around a portion of bone to be stabilized.

7. The system of claim 6, wherein the divider includes a gap through which the first and second surfaces contact one another.

8. The system of claim 6, wherein one of the first and second lumens includes a bulge aligned with the gap to urge the corresponding one of the proximal and distal portions of the longitudinal element received therein into contact with the other of the proximal and distal portions.

9. The system of claim 1, wherein the bone fixation element includes a bone plate and a locking block, the locking block being coupleable within a hole in the bone plate, the channel extending through the locking block.

10. The system of claim 1, wherein the bone fixation element is one of a bone screw and a bone pin wherein the channel extends through a head thereof.

11. The system of claim 1, wherein the bone fixation element is a pedicle screw including a recess shaped to receive a bone fixation rod about which the longitudinal element is to be secured.

12. A device for securing a bone cerclage member to a bone, comprising:
    a bone fixation element including a channel extending therethrough sized and shaped to slidably receive therein an elongated portion of the bone cerclage member, a longitudinal axis of the channel being angled relative to a longitudinal axis of the bone fixation element, the bone fixation element including a recess having a first opening sized and shaped to receive an enlarged head of the bone cerclage member and a second opening sized and shaped to prevent the enlarged head from being out of the channel therethrough, the channel being configured so that when the bone cerclage member is passed therethrough, looped around a target bone and reinserted through the channel, a proximal portion of the bone cerclage member frictionally engages a distal portion of the bone cerclage member within the channel.

13. The device of claim 12, wherein the channel includes a divider separating a first lumen in which the proximal portion of the bone cerclage member is received from a second lumen into which the distal portion of the bone cerclage member is inserted after being wrapped around the target portion of bone to be stabilized.

14. The device of claim 13, wherein the divider includes a gap through which the proximal and distal portions of the bone cerclage member contact one another.

15. The device of claim 13, wherein one of the first and second lumens includes a bulge configured to urge the predetermined portions of the proximal and distal portions of the bone cerclage member into contact with one another.

16. The device of claim 12, wherein the bone fixation element is a locking block insertable into a further comprising a locking block insertable into a bone plate in an operative configuration, the locking block being configured so that insertion of the locking block into the bone plate locks a position of the bone cerclage member inserted therethrough.

17. The device of claim 12, wherein the bone fixation element is one of a bone screw and a bone pin wherein the channel extends through a head thereof.

18. The device of claim 12, wherein the bone fixation element is a pedicle screw including a recess shaped to receive a bone fixation rod about which the longitudinal element is to be secured.

* * * * *